US00PP37342P3

(12) United States Plant Patent
MacGregor et al.

(10) Patent No.: US PP37,342 P3
(45) Date of Patent: Mar. 24, 2026

(54) ***GEUM* PLANT NAMED 'MACGEU050'**

(50) Latin Name: *Geum*
Varietal Denomination: MACGEU050

(71) Applicants: Alasdair MacGregor, Kirkcudbright (GB); Elizabeth MacGregor, Kirkcudbright (GB); John MacGregor, Kirkcudbright (GB)

(72) Inventors: Alasdair MacGregor, Kirkcudbright (GB); Elizabeth MacGregor, Kirkcudbright (GB); John MacGregor, Kirkcudbright (GB)

(73) Assignee: Elizabeth MacGregor's Nursery, Kirkcudbright (GB)

( * ) Notice: Subject to any disclaimer, the term of this patent is extended or adjusted under 35 U.S.C. 154(b) by 0 days.

(21) Appl. No.: 18/831,136

(22) Filed: Aug. 13, 2024

(65) Prior Publication Data

US 2025/0063960 P1 Feb. 20, 2025

(30) Foreign Application Priority Data

Aug. 15, 2023 (QZ) ..... PBR 2023/1680

(51) Int. Cl.
*A01H 5/02* (2018.01)
*A01H 6/06* (2018.01)
*A01H 6/74* (2018.01)

(52) U.S. Cl.
USPC ..... Plt./263.1
CPC ..... *A01H 6/06* (2018.05)

(58) Field of Classification Search
USPC ..... Plt./263.1
CPC ..... A01H 5/02; A01H 5/00; A01H 6/74
See application file for complete search history.

(56) References Cited

PUBLICATIONS

CPVO Community Plant Variety Office Version 4.21.9 retrieved on Dec. 17, 2024 at https://online.plantvarieties.eu/public-ConsultationDetails?registerId=20231680&denomination=macgeu050, 3 pp. (Year: 2024).*
Florali Licensing B.V. *Geum* Solar Tempest Macgeu050, retrieved on Dec. 18, 2024 at https://florali.biz/en/varieties/995/geum_solar_tempest_macgeu050, 3 pp. (Year: 2024).*
Hawke A Comparative Evaluation Study of *Geum* spp. Plant Evaluation Notes, Issue 41, 2017, 1-10. (Year: 2017).*
Instagram Ashton Hall Garden Centre retrieved on Dec. 18, 2024 at https://www.instagram.com/ashtonhallgardencentre/p/CsVxl8yK2pl/, 2 pp. (Year: 2023).*
RHS *Geum* Lady Stratheden (d) retrieved on Dec. 17, 2024 at https://www.rhsplants.co.uk/plants/_/geum-lady-stratheden/classid.2000022988/, 5 pp. (Year: 2024).*

* cited by examiner

*Primary Examiner* — June Hwu
(74) *Attorney, Agent, or Firm* — Samuel R. McCoy, Jr.

(57) ABSTRACT

'MACGEU050' is a new and distinctive variety of *Geum* hybrid which is characterized by a clump-forming growth habit, yellow semi-double flowers held on compound cymes above the foliage, and a long bloom period. The new variety propagates successfully by stem cuttings and tissue culture and has shown to be uniform and stable in the resulting generations from asexual propagation.

3 Drawing Sheets

Latin name of the genus and species: The Latin name of the genus and species of the novel variety disclosed herein is *Geum* species.

Variety denomination: The inventive variety of *Geum* hybrid disclosed herein has been given the variety denomination 'MACGEU050'.

CROSS REFERENCE TO RELATED APPLICATIONS

This application claims priority to the Community Plant Variety Rights application number 2023/1680, filed Aug. 15, 2023, which is herein incorporated by reference.

BACKGROUND OF THE INVENTION

Parentage: 'MACGEU050' is the result of a controlled cross-pollination breeding program carried out by the inventors at their commercial nursery in Kirkcudbright, Scotland, in 2015 and 2016. The inventors performed a controlled cross-pollination of the emasculated seed parent, *Geum chiloense* 'Lady Strathedon' (unpatented), with an unnamed, yellow-flowered *Geum* sp. plant. The unnamed pollen parent was developed and is owned by the inventor and was never made available to the public. Said pollination was performed in an insect proof environment. Seed from said cross was harvested, then germinated, and the resulting seedlings were then grown to a mature size in a protected poly tunnel greenhouse. In 2018, the inventors selected the new *Geum* cultivar for its unique flower and bloom characteristics. This new and distinctive cultivar was given the name 'MACGEU050'.

Asexual Reproduction: Asexual reproduction of 'MACGEU050' was first accomplished in 2019 by way of meristematic tissue culture micro propagation at a laboratory in Rijswijk, the Netherlands. Three successive generations have shown that the unique features of the instant cultivar are stable and reproduce true to type.

SUMMARY OF THE INVENTION

The cultivar 'MACGEU050' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Geum* cultivar, 'MACGEU050'.

1. *Geum* 'MACGEU050' exhibits a clump-forming growth habit; and
2. *Geum* 'MACGEU050' exhibits semi-double yellow flowers arranged in compound cymes held above the foliage; and
3. *Geum* 'MACGEU050' exhibits a long bloom period, from April through July in Kirkcudbright, Scotland.

BOTANICAL DESCRIPTION OF THE PLANT

Figure 1:
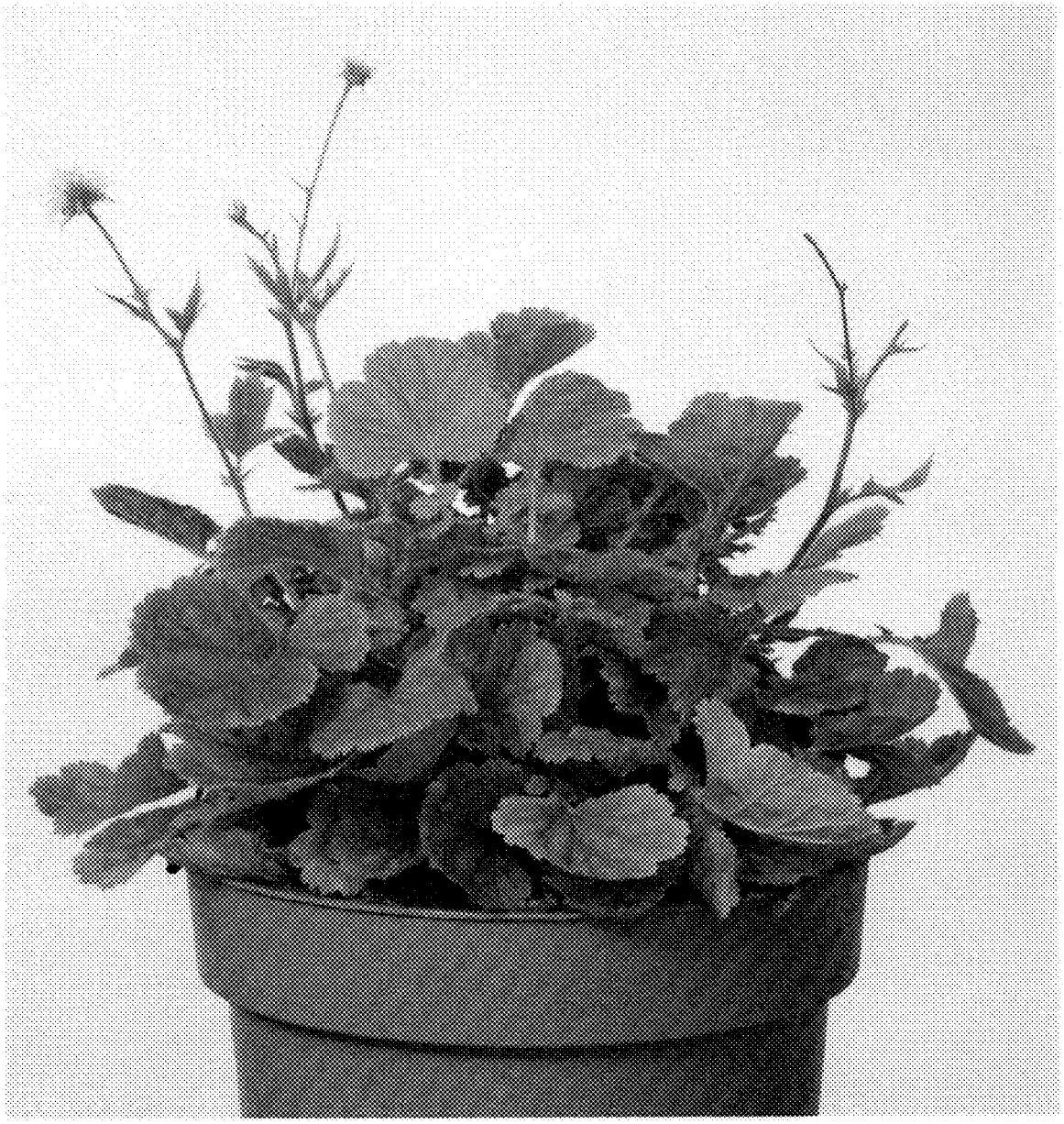
FIG. 1 shows, as nearly true as it is reasonably possible to make the same in color illustrations of this type, the typical foliage and growth characteristics of the new cultivar, 'MACGEU050'. The plant shown is approximately three-month-old, potted into a 19 cm nursery container, grown outdoors in Kirkcudbright, Scotland at a commercial nursery.
Figure 2:
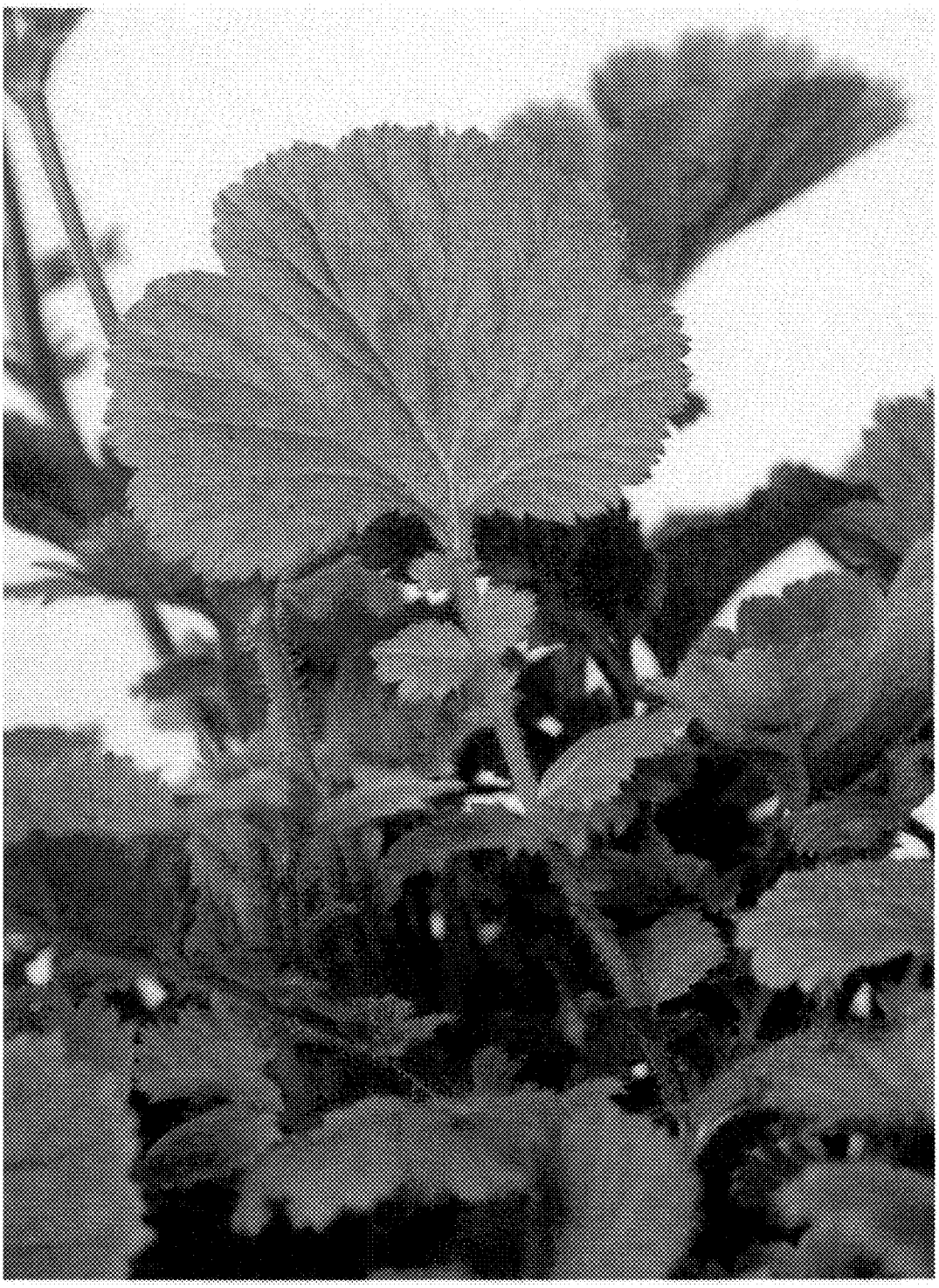
FIG. 2 shows, as nearly true as it is reasonably possible to make the same in color illustrations of this type, the typical foliage of the claimed plant.
Figure 3:
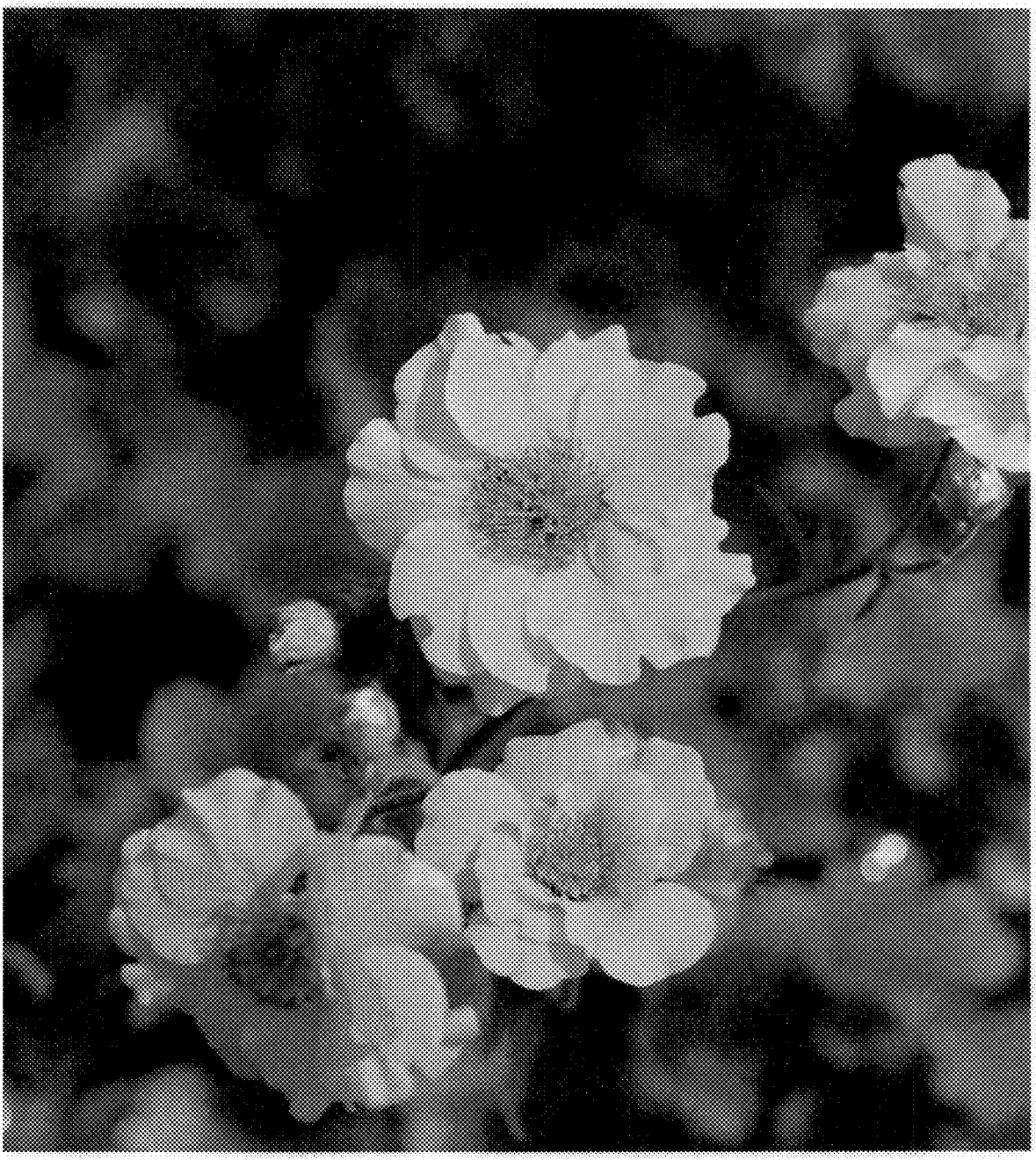
FIG. 3 shows, as nearly true as it is reasonably possible to make the same in color illustrations of this type, the typical flower of the claimed plant.

The following is a detailed botanical description of a new and distinct variety of *Geum* known as 'MACGEU050', based upon observations of 3-month-old greenhouse-grown plants grown in Kirkcudbright, Scotland. Plants were grown using conventional greenhouse production protocols for *Geum* plants including regular overhead irrigation, fertigation feeding, and full sun to partial shade exposure. With the exception of chemical control for thrips insects, no other chemical treatments were given to the plants. Observation data was recorded in July of 2024.

Those skilled in the art will appreciate that certain characteristics will vary with older or, conversely, with younger plants. 'MACGEU050' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2007 edition.

A botanical description of 'MACGEU050' and comparisons with the seed parent and most similar variety of common knowledge are provided below.

General plant description:

*Growth habit*.—A clump-forming herbaceous perennial with flowering stems arising from the base and no lateral branching present.

*Height*.—13.5 cm to the top of the foliar plane; 19.9 cm to the top of the floral plane.

*Spread*.—27.4 cm.

*Plant vigor*.—Moderate.

*Growth rate*.—Moderate.

*Propagation*.—Meristematic tissue culture.

*Time to produce flowering plant from rooted cutting*.—At 8 to 10 degrees Celsius, approximately 8 to 10 weeks from a tissue culture to a saleable 17 cm pot; no pinching is required.

*Pest resistance and susceptibility*.—Not any more or less susceptible to pests or diseases known to effect *Geum*.

*Environmental tolerances*.—Adapt to, at least, USDA Zones 5 to 9 and temperatures ranging from minus 25 degrees Celsius to 35 degrees Celsius; low to moderate tolerance to rain; moderate to high tolerance to wind.

Root system: Thin, fibrous, and freely branched.

Stem:

*Branching habit*.—Basally branched; freely branching.

*Number of primary (main) stems per plant*.—16.

*Number of secondary (lateral) branches per plant*.—None.

*Appearance and shape*.—Terete.

*Length*.—13.4 cm.

*Diameter*.—0.2 cm.

*Internode length*.—3.5 cm.

*Luster*.—Slightly glossy.

*Aspect*.—Average angle of 15 degrees from vertical; stems vary from between 0 to 30 degrees from vertical.

*Strength*.—Strong.

*Color, juvenile*.—Yellow-green, nearest to RHS 145A.

*Color, mature*.—Yellow-green, nearest to RHS 144A.

*Color at internodes*.—Yellow-green, nearest to RHS 144A.

*Pubescence*.—Densely pubescent; hairs are soft, white RHS NN155D, and 1.0 mm long, on average.

Foliage:

*Arrangement*.—Leaves are borne both basally and on stems; on stems, arrangement is alternate.

*Basal leaves*.—Attachment — Petiolate. Division — Imparipinnate with an average of 10 leaflets. Leaf shape — Compound leaf outline is obovate. Dimensions — 15.4 cm long, including petiole, and 5.3 cm in width, on average. Leaf attitude — Outward and upward. Leaf aspect — Carinate. Leaflets — Quantity — Typically ranging from 9 to 11 leaflets per leaf. Dimensions, terminal leaflet — 4.7 cm long and 5.3 cm wide. Dimensions, lateral leaflets — 1.1 cm long and 0.9 cm wide. Shape, terminal leaflet — Reniform and trilobate though occasionally five-lobed; deeply cleft to near-parted; divergent; sinus depth is shallow to moderately deep. Shape, lateral leaflets — Broad ovate. Apex — Abruptly acute. Leaf base — Truncate. Leaf margin — Serrate. Texture, adaxial and abaxial surfaces — Smooth, pubescent. Pubescence, adaxial and abaxial surfaces — Soft, strigose hairs with an average length of 1.0 mm; colored near RHS NN155D. Luster, adaxial and abaxial surfaces — Matte. Color — Juvenile foliage color, adaxial surface — Yellow-green, RHS 144A. Juvenile foliage color, abaxial surface — Yellow-green, RHS 146D. Mature leaf color, adaxial surface — Green, RHS 137D. Mature leaf color, abaxial surface — Yellow-green, nearest to a mixture of RHS 144A and 146C. Venation — Type — Pinnate. Vein color, adaxial surface — Green, RHS 137D. Vein color, abaxial surface — Yellow-green, RHS 146D.

*Petiole*.—Length — 12.2 cm, including rachis. Diameter — Average of 0.2 cm. Strength — Moderately strong to strong. Color, adaxial surface — Green, RHS 143B. Color, abaxial surface — Yellow-green, RHS 144B. Texture, adaxial and abaxial surfaces — Densely covered with soft hairs; average length of hairs is 1.0 mm; colored white, RHS NN155D. Luster, adaxial surface — Matte. Luster, abaxial surface — Slightly glossy. Stipules — None present.

*Leaves borne on the stems*.—Quantity — Approximately 4 leaves per stem. Attachment — Petiolate. Division — Simple. Leaf shape — Trilobate with a broad ovate outline. Lobes — Depth of sinuses — Deep to nearly parted. Sinus orientation — Divergent. Dimensions — 4.1 cm long, including petiole, and 3.0 cm in width, on average. Leaf attitude — Leaves in an average angle of 45 degrees to the stem. Leaf aspect — Flat. Leaf apex — Narrow acute to acute. Leaf base — Attenuate. Leaf margin — Serrate. Texture, adaxial and abaxial surfaces — Smooth, pubescent. Pubescence, adaxial and abaxial surfaces — Soft, strigose hairs with an average length of 1.0 mm; colored near RHS NN155D. Luster, adaxial and abaxial surfaces — Matte. Color — Juvenile foliage color, adaxial surface — Yellow-green, RHS 144B. Juvenile foliage color, abaxial surface — Yellow-green, RHS 144C. Mature leaf color, adaxial surface — Green, RHS 137D. Mature leaf color, abaxial surface — Yellow-green, nearest to a mixture of RHS 144A and 146C. Venation — Type — Pinnate. Vein color, adaxial surface — Green, RHS 137C. Vein color, abaxial surface — Yellow-green, RHS 146D. Petiole — Length — 1.0 cm. Diameter — Average of 1.0 mm. Strength — Medium to high. Color, adaxial surface — Green, nearest to RHS 143B. Color, abaxial surface — Yellow-green, nearest to RHS 144C. Texture, adaxial and abaxial surfaces — Densely covered with soft hairs; average length of hairs is 1.0 mm; colored white, RHS NN155D. Luster, adaxial surface — Matte. Luster, abaxial surface — Slightly glossy. Stipules — General — Two leafy stipules present at the base of each leaf. Shape — Ovate to obovate. Length — Average of 7.0 mm. Diameter — Average of 4.0 mm. Apex — Narrow acute. Base — Cuneate. Margins — Serrate. Color, adaxial surface — Green, nearest to RHS 143B. Color, abaxial surface — Yellow-green, nearest to RHS 144C. Texture, adaxial and abaxial surfaces — Covered with soft, appressed hairs with an average length of 1.0 mm; colored white, RHS NN155D.

Inflorescence:

*Habit*.—Compound cyme.

*Natural flowering season*.—April to mid-summer in Kirkcudbright, Scotland.

*Time to flower or response time*.—Approximately 9 months.

*Dimensions*.—8.1 cm high, including peduncle, and 6.5 cm in diameter.

*Quantity of inflorescence per plant*.—4, on average.

*Quantity of flowers and buds per inflorescence*.—24, on average.

*Peduncles*.—Length — Average of 8.2 cm. Diameter — Average of 2.0 mm. Angle — Average angle to stem is 30 degrees. Strength — Moderately strong to strong. Texture — Smooth and densely pubescent; hairs are soft with an average length of 1.0 mm; colored white, RHS 155A. Luster — Slightly glossy. Color — Yellow-green, RHS 145A, with the upper side tinged greyed-orange, RHS 177A.

*Pedicels*.—Length — Average of 3.3 cm. Diameter — Average of 0.1 cm. Angle — Average angle to peduncle is approximately 10 degrees. Strength — Moderately strong. Texture — Smooth and densely pubescent; hairs are soft with an average length of 0.75 cm; colored white, RHS NN155D. Luster — Slightly glossy. Color — Yellow-green, nearest to RHS 144A.

Flower buds:

*Shape*.—Deltoid.

*Length*.—Average of 5 mm.

*Diameter*.—Average of 6 mm.

*Texture*.—Smooth and densely pubescent; hairs are soft with an average length of 0.5 mm; colored white, RHS 155A.

*Luster*.—Matte.

*Color*.—Yellow-green, RHS 154C; immature calyx is yellow-green, nearest to a mixture of RHS 145A and 145B.

Flower:

*Shape, type*.—Rotate; semi-double.

*Floriferousness*.—Moderately free-flowering.

*Aspect*.—Outwardly to slightly upright.

*Flower longevity on plant*.—Approximately ten days.

*Persistent or self-cleaning*.—Self-cleaning.

*Fragrance*.—Non-fragrant.

*Diameter*.—Average of 3.2 cm.

*Depth*.—Average of 1.1 cm.

*Calyx*.—Shape — Rotate. Length — 0.5 cm. Diameter — 1.3 cm. Sepal — Arrangement — Rotate; one whorl of sepals which alternate between broad sepals and narrow sepals. Quantity — 10 unfused sepals; 5 broad sepals and 5 narrow sepals. Broad sepals — Shape — Deltoid. Aspect — Strongly reflexed. Dimensions — 0.8 cm long and 0.5 cm wide. Apex — Long apiculate. Base — Truncate. Margin — Entire. Texture, upper surface — Smooth; densely covered with soft appressed hairs. Luster, upper surface — Very slightly glossy. Texture, lower surface — Smooth; densely covered with soft appressed hairs. Luster, lower surface — Matte. Color — When opening, upper surface — Yellow-green, RHS 145B. When opening, lower surface — Yellow-green, RHS 145A. Fully opened, upper surface — Yellow-green, RHS 145B. Fully opened, lower surface — Yellow-green, RHS 145A. Narrow sepals — Shape — Narrow elliptic. Dimensions — 0.2 cm long and 0.1 cm wide. Apex — Narrow acute. Base — Attenuate. Sepal reflex — Slightly reflexed to outwardly. Margin — Entire. Texture, upper surface — Smooth; densely covered with soft appressed hairs. Luster, upper surface — Very slightly glossy. Texture, lower surface — Smooth; densely covered with soft appressed hairs. Luster, lower surface — Matte. Color — When opening, upper surface — Yellow-green, RHS 146D. When opening, lower surface — Yellow-green, nearest to in between RHS 146C and 146D. Fully opened, upper surface — Yellow-green, RHS 146D. Fully opened, lower surface — Yellow-green, nearest to in between RHS 146C and 146D.

*Petals*.—Quantity — 11, on average. Arrangement — Rotate; arranged in three whorls of unfused petals. Length — 1.5 cm, on average. Width — 1.3 cm, on average. Shape — Broad obovate. Apex — Emarginate to obtuse. Base — Broad acuminate. Margin — Entire; slight undulation. Texture and luster, upper surface — Glabrous, slightly coriaceous, and matte. Texture and luster, lower surface — Glabrous, slightly coriaceous, and matte. Petal color — When opening, upper surface — Yellow, nearest to RHS 13A. When opening, lower surface — Yellow, nearest to RHS 13C. Fully opened, upper surface — Yellow, nearest to RHS 13B. Fully opened, lower surface — Yellow, nearest to RHS 13C. Petal venation color — Fully opened, upper surface — Yellow-orange, nearest to RHS 14A. Fully opened, lower surface — Yellow, nearest to RHS 11A.

Reproductive organs:

*Stamens*.—Quantity — Approximately 150.Anthers — Shape — Oblong. Dimensions — Approximately 0.8 mm long and 0.3 mm wide. Color — Yellow-orange, RHS 14A. Filaments — Length — 4 mm, on average. Color — Green-yellow, RHS 1B to 1C, and fading to yellow, RHS 12B to 12C; distal portion fading to RHS 28C to 28D when maturing. Pollen — Not detected.

*Pistil*.—Quantity — 60, on average. Length — 0.6 mm. Style — Length — 5.5 mm. Color — Red, RHS 42D. Stigma — Shape — Cleft; two-parted. Length — 0.5 mm. Diameter — 0.8 mm. Color — Red, RHS 53A. Ovary Color — Yellow-green, RHS 144A.

Seed and fruit: No fruit or seeds have been detected to date.

COMPARISONS WITH THE PARENT PLANTS AND MOST SIMILAR VARIETY OF COMMON KNOWLEDGE

Plants of the new cultivar 'MACGEU050' differ from its seed parent, *Geum chiloense* 'Lady Strathedon' (unpatented), by the characteristics described in Table 1. The pollen parent is no longer available for comparison.

TABLE 1

Comparison Between The 'MACGEU050' and the Seed Parent

| Characteristic | 'MACGEU050' | 'Lady Strathedon' |
|---|---|---|
| Petal count. | Lower than 'Lady Strathedon'; semi-double. | Higher than 'MACGEU050'; double. |
| Bloom period. | Earlier than 'Lady Strathedon'; April through July. | Later than 'MACGEU050'; June through August. |
| Bloom period duration. | Longer than 'Lady Strathedon'; approximately four months, from April through July. | Shorter than 'MACGEU050'; approximately 3 months, from June through August |

Plants of the new cultivar 'MACGEU050' may be distinguished from the most similar known commercial comparator, *Geum* 'Lisanne' (not patented), by the characteristics described in Table 2.

TABLE 2

Comparison Between The 'MACGEU050' and 'Lisanne'

| Characteristic | 'MACGEU050' | 'Lisanne' |
|---|---|---|
| Plant height. | Taller than 'Lisanne'. | Shorter than 'MACGEU050'. |
| Growth habit. | Clumping. | Vigorously spreading habit. |
| Bloom period duration. | Longer than 'Lisanne'; early spring to mid-summer. | Shorter than 'MACGEU050'; mid-spring to late spring. |

That which is claimed is:

1. A new and distinct variety of *Geum* hybrid plant named 'MACGEU050', substantially as described and illustrated herein.

* * * * *